US00PP21749P2

(12) United States Plant Patent
Pieters

(10) Patent No.: US PP21,749 P2
(45) Date of Patent: Mar. 1, 2011

(54) *CHRYSANTHEMUM* PLANT NAMED 'PPP MORA 09'

(50) Latin Name: *Chrysanthemum morifolium*
Varietal Denomination: PPP MORA 09

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 11 days.

(21) Appl. No.: 12/462,281

(22) Filed: Aug. 1, 2009

(51) Int. Cl.
*A01H 5/00* (2006.01)

(52) U.S. Cl. ..... Plt./292

(58) Field of Classification Search ..... Plt./292
See application file for complete search history.

(56) References Cited

U.S. PATENT DOCUMENTS

PP10,207 P * 1/1998 Pieters ..... Plt./286
PP13,794 P3 * 5/2003 Pieters ..... Plt./287
PP14,501 P3 * 2/2004 Pieters ..... Plt./292

* cited by examiner

*Primary Examiner*—Wendy C. Haas
(74) *Attorney, Agent, or Firm*—Mark Bourgeois

(57) ABSTRACT

A new and distinct *Chrysanthemum* plant cultivar is disclosed, characterized by large decorative type inflorescences, consistent flowering response to short days, blooming consistently after 49 days of short day length, dark pink ray florets, free branching habit, and a consistent natural season flowering habit during the second week of August.

1 Drawing Sheet

Latin name of the genus and species: *Chrysanthemum morifolium.*

Variety denomination: 'PPP MORA 09'.

BACKGROUND OF THE INVENTION

The new cultivar 'PPP MORA 09' is a product of a cross between the male parent 'GEDI ONE CAR' (U.S. Plant Pat. No. 13,794) and the female parent 'Tripoli' (U.S. Plant Pat. No. 10,207). The new cultivar was discovered and selected by Dirk Pieters in October of 2001 in a greenhouse in Oostnieuwkerke, Belgium.

Asexual reproduction of the new cultivar 'PPP MORA 09' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP MORA 09' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP MORA 09.' These characteristics in combination distinguish 'PPP MORA 09' as a new and distinct *Chrysanthemum* cultivar:

1. Large, dark pink, decorative-type inflorescences;
2. Consistent natural season flowering habit during the second week of August;
3. Free branching habit; and
4. Consistent flowering response to short days, blooming consistently after 49 days of short day length.

Plants of the new cultivar 'PPP MORA 09' are similar to plants of the male parent variety, 'GEDI ONE CAR' in most horticultural characteristics, however plants of the new cultivar 'PPP MORA 09' are shorter with a wider plant spread. Also, the new cultivar 'PPP MORA 09' has a smaller inflorescence diameter and longer inflorescence longevity. Additionally, the ray florets of 'PPP MORA 09' are a much lighter purple. Finally, 'PPP MORA 09' naturally blooms one to two weeks earlier than the male parent 'GEDI ONE CAR'.

Plants of the new cultivar 'PPP MORA 09' are similar to plants of the female parent variety, 'Tripoli' in most horticultural characteristics, however plants of the new cultivar 'PPP MORA 09' are shorter but have a wider plant spread. Also, the new cultivar 'PPP MORA 09' has decorative inflorescences compared to the daisy inflorescences of the female parent. Additionally, 'PPP MORA 09' has a larger inflorescence diameter. Finally, 'PPP MORA 09' naturally blooms one week earlier than the female parent 'Tripoli'.

In comparison to the commercially available variety 'GEDI TWO PAD' (U.S. Plant Pat. No. 14,501), 'PPP MORA 09' is smaller in both height and plant spread. Additionally, the new variety 'PPP MORA 09' blooms two to three weeks later. Further, the new variety 'PPP MORA 09' has a larger inflorescence diameter and the ray florets are darker purple in color. Finally, 'PPP MORA 09' has longer inflorescence longevity.

BRIEF DESCRIPTION OF THE PHOTOGRAPH

The accompanying photograph in the drawing illustrates in full color a typical plant of 'PPP MORA 09' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP MORA 09' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP MORA 09'.

Commercial classification: Garden-type *Chrysanthemum.*

PROPAGATION

Time to rooting: 7 to 14 days at approximately 21° C.

Root description: Fine, fibrous.

PLANT

Growth habit: Mounding herbaceous perennial.

Height: Approximately 15 cm.

Plant spread: Approximately 29 cm.

Growth rate: Moderate.

Branching characteristics: Free Branching.

Length of lateral branches: Approximately 11 cm.

Number of leaves per lateral branch: Approximately 24.

Age of plant described: Approximately 139 days.

FOLIAGE

Leaf:

- *Arrangement.*—Alternate single.
- *Average length.*—Approximately 4.2 cm.
- *Average width.*—Approximately 3.9 cm.
- *Shape of blade.*—Ovate.
- *Apex.*—Acuminate.
- *Base.*—Attenuate.
- *Attachment.*—Stalked.
- *Margin.*—Serrate.
- *Texture of top surface.*—Lightly pubescent.
- *Texture of bottom surface.*—Lightly pubescent.
- *Leaf internode length.*—Approximately 1.2 cm.
- *Color.*—Young foliage upper side: Near Green 137A. Young foliage under side: Near Green 138A. Mature foliage upper side: Near Green 137B. Mature foliage under side: Near Green 138B.
- *Venation.*—Type: Palmately net. Venation color upper side: Near Green 138B. Venation color under side: Near Green 138C.

Petiole:

- *Average length.*—Approximately 2.6 cm.
- *Color.*—Near Green 138B.
- *Diameter.*—Approximately 0.3 cm.

BLOOM

Inflorescence:

- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the third week in September.
- *Number of inflorescences per lateral branch.*—Approximately 8.
- *Inflorescence diameter.*—Approximately 5.1 cm.
- *Inflorescence depth.*—Approximately 1.9 cm.
- *Inflorescence longevity on plant.*—Approximately 26 to 34 days.
- *Persistence.*—Persistent.

Ray florets:

- *Appearance.*—Matte.
- *Texture.*—Smooth.
- *Average number of ray florets per inflorescence.*—210.
- *Shape.*—Oblanceolate, reflexed.
- *Aspect.*—Flat.
- *Margin.*—Entire.
- *Apex.*—Obtuse.
- *Base.*—Fused along 20% of length.
- *Average length.*—Approximately 2 cm.
- *Average width.*—Approximately 0.7 cm.
- *Color.*—Upper surface at first opening: Near Red-Purple 61A. Upper surface at maturity: Near Red-Purple 74C. Upper surface at fading: Near Red-Purple 74D. Under surface at first opening: Near Red-Purple 61A. Under surface at maturity: Near Red-Purple 74D. Under surface at fading: Near Red-Purple 74D.

Disc florets:

- *Appearance.*—Shiny.
- *Texture.*—Smooth.
- *Average number of florets per disc.*—Approximately 2.
- *Shape.*—Cylindric.
- *Apex.*—Obtuse.
- *Average length.*—Approximately 0.2 cm.
- *Average width.*—Approximately 0.1 cm.
- *Color.*—At first opening: Near Yellow-Green 154C. At maturity: Near Yellow 13A. At fading: Near Yellow 13A.

Peduncle:

- *Length.*—At terminal end (shortest): Approximately 2.2 cm. At lateral end (longest): Approximately 6.3 cm.
- *Angle to stem.*—Acute.
- *Strength.*—Moderate.
- *Color.*—Near Green 138C.
- *Habit.*—Upright.
- *Diameter.*—Approximately 0.2 cm.
- *Surface texture.*—Lightly pubescent.

Inflorescence bud:

- *Length.*—Approximately 0.6 cm.
- *Diameter.*—Approximately 0.4 cm.
- *Form.*—Globose.
- *Color.*—Near Red-Purple 61A.

Involucral bracts (phyllaries):

- *Appearance.*—Matte.
- *Texture.*—Lightly pubescent.
- *Number.*—Approximately 30.
- *Shape.*—Lanceolate.
- *Margin.*—Entire.
- *Apex.*—Obtuse.
- *Length.*—Approximately 0.5 cm.
- *Width.*—Approximately 0.2 cm.
- *Color.*—Upper side: Near Green 138B. Under side: Near Green 138B.

REPRODUCTIVE ORGANS

Ray florets:

- *Number of pistils per floret.*—1.
- *Stigma shape.*—2 branched.
- *Stigma color.*—Near Yellow 13A.
- *Style color.*—Near Green-Yellow 1C.
- *Style length.*—Approximately 0.3 cm.
- *Stamens.*—Absent.

Disc florets:

*Number of pistils per floret.*—1.
*Stigma shape.*—Cylindric.
*Stigma color.*—Near Yellow 13A.
*Style length.*—Approximately 0.1 cm.
*Style color.*—Near Green-Yellow 1D.
*Number of stamens per floret.*—Approximately 5.
*Anther shape.*—Tubular.
*Anther color.*—Near Yellow 13A.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP MORA 09' as herein illustrated and described.

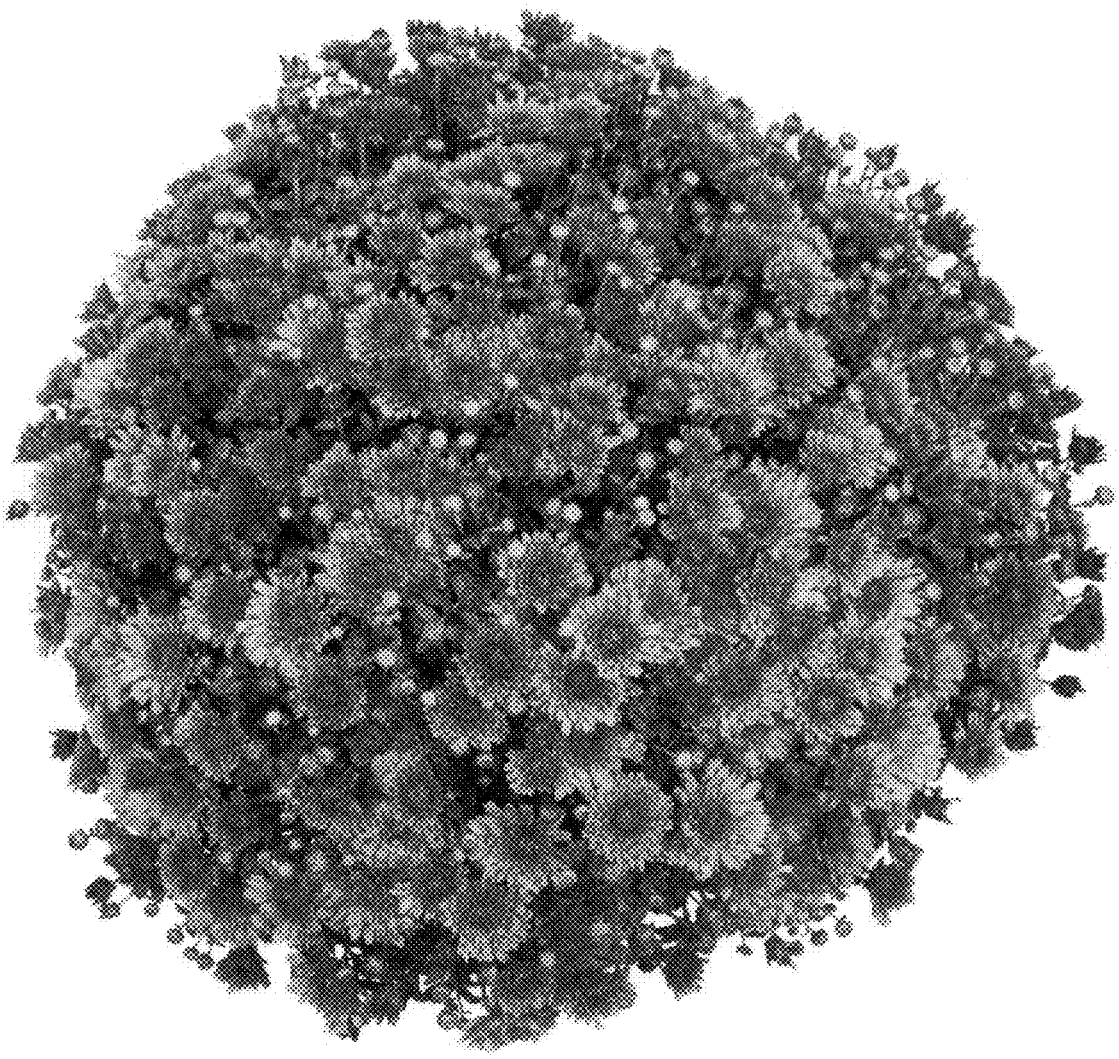

* * * * *